(12) United States Patent
Banker

(10) Patent No.: US 10,773,031 B2
(45) Date of Patent: Sep. 15, 2020

(54) NEEDLE FOR SUBCISION PROCEDURES

(71) Applicant: WLB Interventional, LLC, Maumee, OH (US)

(72) Inventor: Wade Banker, Sylvania, OH (US)

(73) Assignee: WLB Interventional, LLC, Maumee, OH (US)

( * ) Notice: Subject to any disclaimer, the term of this patent is extended or adjusted under 35 U.S.C. 154(b) by 183 days.

(21) Appl. No.: 16/057,271

(22) Filed: Aug. 7, 2018

(65) Prior Publication Data
US 2019/0046738 A1 Feb. 14, 2019

Related U.S. Application Data

(60) Provisional application No. 62/542,979, filed on Aug. 9, 2017.

(51) Int. Cl.
| | |
|---|---|
| *A61B 17/3205* | (2006.01) |
| *A61B 17/3209* | (2006.01) |
| *A61B 17/32* | (2006.01) |
| *A61B 17/00* | (2006.01) |
| *A61M 5/32* | (2006.01) |

(52) U.S. Cl.
CPC ....... *A61M 5/3286* (2013.01); *A61B 17/3205* (2013.01); *A61B 17/32053* (2013.01); *A61B 17/32093* (2013.01); *A61B 2017/00747* (2013.01); *A61B 2017/00761* (2013.01); *A61B 2017/320056* (2013.01)

(58) Field of Classification Search
CPC .......... A61M 5/3286; A61B 17/32053; A61B 17/3205; A61B 17/32093; A61B 2017/00747; A61B 2017/00761; A61B 2017/320056
See application file for complete search history.

(56) References Cited

U.S. PATENT DOCUMENTS

| | | | |
|---|---|---|---|
| 4,365,957 A | 12/1982 | Das | |
| 2007/0005091 A1* | 1/2007 | Zadini | A61B 17/32 606/192 |
| 2013/0123662 A1* | 5/2013 | Hipp | A61B 10/0275 600/564 |
| 2013/0144292 A1* | 6/2013 | To | A61B 17/3205 606/79 |
| 2014/0257272 A1* | 9/2014 | Clark | A61B 18/14 606/37 |
| 2016/0249948 A1* | 9/2016 | Umar | A61B 17/32053 606/133 |

* cited by examiner

*Primary Examiner* — Katrina M Stransky
(74) *Attorney, Agent, or Firm* — MacMillan, Sobanski & Todd, LLC (57) ABSTRACT

Described is a needle for subcision procedures having a concave cutting tip comprising two or more cutting edges wherein the concave cutting tip is at the cutting end of a shaft of the needle and wherein a handle is disposed at an angle relative to the axis defined by the center of the shaft of the needle. The cutting edges may be sharp interior edges within the circumference of the needle.

17 Claims, 6 Drawing Sheets

NEEDLE FOR SUBCISION PROCEDURES

RELATED APPLICATIONS

This application claims priority to U.S. Provisional Application No. 62/542,979, filed under 35 U.S.C. § 111(b) on Aug. 9, 2017, the disclosure of which is expressly incorporated herein by reference in its entirety for all purposes.

BACKGROUND

Three-dimensional collagen bands allow skin to move in multiple directions. Scar tissue grows through these three-dimensional collagen bands, causing a loss of skin flexibility. Subcision procedures break up scar tissue from underneath, preferably without creating new scar tissue, so as to allow the collagen bands to regrow and improve skin flexibility and appearance. However, subcision procedures are not always effective, often requiring multiple procedures.

Currently, the instrument used to perform subcision procedures is a needle without cutting edges. The needle is inserted underneath the skin and the tip of the needle is pushed against the scar tissue to break apart the scar tissue. Because the needle lacks cutting edges, the scar tissue is broken apart purely by the use of force. Therefore, the surgeon performing the subcision procedure must exert considerable force on the needle to ensure the tip of the needle breaks apart the scar tissue. Without a cutting mechanism, a surgeon must repeatedly push the needle through the scar tissue which can cause trauma to the treated area. This trauma can result in considerable swelling and increased recovery time. In addition, the amount of scar tissue broken apart in each pushing motion is limited due to the needle's design in that only the tip of the needle breaks apart the scar tissue. The dull sides of the needle just push the rest of the scar tissue to the side to be treated in the next pass of the needle. As a result, a surgeon must repeatedly move the needle in a back-and-forth motion to break apart all the scar tissue, and more passes of the needle means more time to complete the procedure.

In addition, current subcision procedures are performed with a needle that proceeds in a straight plane from the needle tip to the handle. Such an instrument requires the surgeon performing the procedure to have to pull and manipulate a patient's skin in order to access the scar tissue. This takes time and energy and can be inexact, which complicates the procedure. Thus, there is a need in the art for new and improved tools and methods for performing subcision procedures that are safer, quicker, and easier to perform while also increasing the efficacy of the procedure.

SUMMARY

Provided herein is a needle comprising a shaft defining an axis and extending between a base end and a cutting end, a handle disposed on the base end at an angle relative to the axis, and a concave cutting tip at the cutting end, wherein an outer surface of the concave cutting tip defines a circumference, and the concave cutting tip comprises a first cutting edge defined by a first recessed face extending from a first edge base to a first terminus point, and a second cutting edge defined by a second recessed face extending from a second edge base to a second terminus point, wherein the first cutting edge and the second cutting edge are each within the circumference. In certain embodiments, the angle ranges from about 5 degrees to about 50 degrees. In certain embodiments, the angle ranges from about 15 degrees to about 45 degrees. In certain embodiments, the angle is about 30 degrees.

In certain embodiments, the first edge base and the second edge base meet to define a confluence point. In particular embodiments, the confluence point defines a V-shaped apex between the first cutting edge and the second cutting edge. In certain embodiments, the shaft is non-hollow. In certain embodiments, the shaft is hollow.

In certain embodiments, the needle has a diamaeter corresponding to an 18-gauge or a 20-gauge needle.

In certain embodiments, the first cutting edge and the second cutting edge are each concave with respect to the axis.

In certain embodiments, the first and second terminus points are at the ends of curled tips.

In certain embodiments, the first edge base and the second edge base do not meet at a confluence point. Instead, a door is located between the first edge base and second edge base to introduce substances into an anatomical location or to collect excised scar tissue debris.

In other embodiments, the concave cutting tip includes multiple concavities wherein the concave cutting tip comprises first, second, third, and fourth cutting edges, wherein an outer surface of the concave cutting tip defines a circumference, and the concave cutting tip comprises a first cutting edge defined by a first recessed face extending from a first edge base to a first terminus point, a second cutting edge defined by a second recessed face extending from a second edge base to a second terminus point, a third cutting edge defined by a third recessed face extending from a third edge base to a third terminus point, and a fourth cutting edge defined by a fourth recessed face extending from a fourth edge base to a third terminus point, wherein the third terminus point is formed by the convergence of the third cutting edge with the fourth cutting edge.

In certain embodiment, the third terminus point is recessed from the first and second terminus points.

Also provided herein is a needle comprising a shaft defining an axis and extending between a base end and a cutting end, a handle disposed on the base end at an angle relative to the axis, and a convex cutting tip at the cutting end, wherein an outer surface of the convex cutting tip defines a circumference, and the convex cutting tip comprises a first cutting edge defined by a first recessed face extending from a first edge base to a first terminus point and a second cutting edge defined by a second recessed face extending from a second edge base to a first terminus point, wherein the first terminus point is formed by the convergence of the first cutting edge with the second cutting edge, and wherein the first cutting edge and the second cutting edge are each within the circumference.

Further provided is a method of performing a subcision procedure, the method comprising using a needle described herein to perform a subcision procedure on a patient.

Further provided is a method of performing a subcision procedure, the method comprising holding a needle having a cutting tip by a handle connected to the needle at an angle thereto, and inserting the needle into skin of a patient at an acute angle adjacent to a scar with the cutting tip substantially parallel to a skin surface, where the cutting tip comprises two or more sharp cutting edges interior to a circumference of the needle, advancing and moving the needle in a fan-like motion through the dermis so as to transect fibrous bands in the dermis with the cutting edges, rotating the needle and moving the needle in a fan-like motion through the scar, and removing the needle from the skin of the patient.

In certain embodiments, the method further comprises a step of cleaning an area around the skin prior to inserting the needle. In certain embodiments, the method further comprises defining margins of the scar prior to inserting the needle. In certain embodiments, the method further comprises administering a local anaesthetic to the patient prior to inserting the needle. In certain embodiments, the subcision procedure is a procedure to remove acne scars. In certain embodiments, the needle is squeezed circumferentially around an exit point to prevent large haematoma formation due to bleeding. In certain embodiments, the method further comprises applying pressure to the skin where the needle was removed for a period of time.

Use of a needle including one or more cutting edges as described herein may reduce trauma to the surgical area and may beneficially result in a safer and quicker procedure with less swelling.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIGS. 3A-3B: Views of the cutting edges as seen from the perspective of the axis α looking toward the concave cutting tip.

FIGS. 4A-4D: Non-limiting illustrations of embodiments of a concave cutting tip, where first and second cutting edges do not meet at a confluence point (FIG. 4A), and where first and second cutting edges meet at a confluence point (FIGS. 4B-4D).

FIGS. 6A-6B: Non-limiting illustrations of an embodiment of a concave cutting tip where the first and second edge bases do not meet at a confluence point and a door is contained in the interior of the concave cutting tip.

FIGS. 7A-7E: Non-limiting illustrations of embodiments of a concave cutting tip having four cutting edges that define multiple concavities.

FIGS. 8A-8B: Non-limiting illustrations of embodiments of a convex cutting tip.

DETAILED DESCRIPTION

Subcision, also referred to as subcutaneous incisional surgery, is a surgical procedure for the treatment of depressed cutaneous scars and wrinkles. In a subcision procedure, a needle is used to break fibrotic strands that tether the scar to the underlying tissue. The release of these fibrotic strands, and new collagen deposition caused by wound healing, results in cosmetic improvement of the scar. The broken scar tissue then dissolves. Provided herein is a needle that provides various advantages in performing subcision procedures.

Referring now to FIGS. 1-5, a needle 10 for subcision procedures includes a shaft 12 and a handle 14, where the shaft 12 extends from a base end 16 to a cutting end 18. The center of the shaft 12 defines an axis α. The shaft 12 generally has the size of an 18-gauge or 20-gauge needle, though other shaft sizes are possible. The preferred shaft size depends on various factors such as the particular procedure being peformed with the needle 10, the anatomical location of the procedure being performed, and the surgeon's preferences. The shaft 12 can be hollow like conventional needles, in which case a central bore 20 runs along the axis α, or can be solid (i.e., non-hollow). The shaft 12 can be manufactured out of stainless steel, or other materials capable of being sterilized and otherwise suitable for use in surgical instruments.

Figure 1:
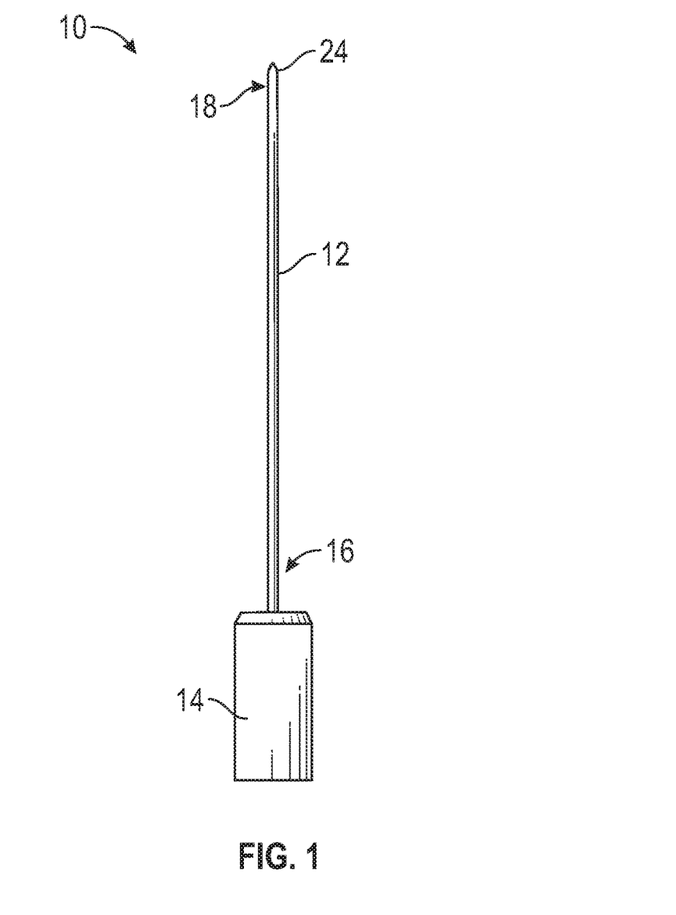
FIG. 1: Non-limiting schematic illustration of a needle for subcision procedures as seen from the top.
Figure 2:
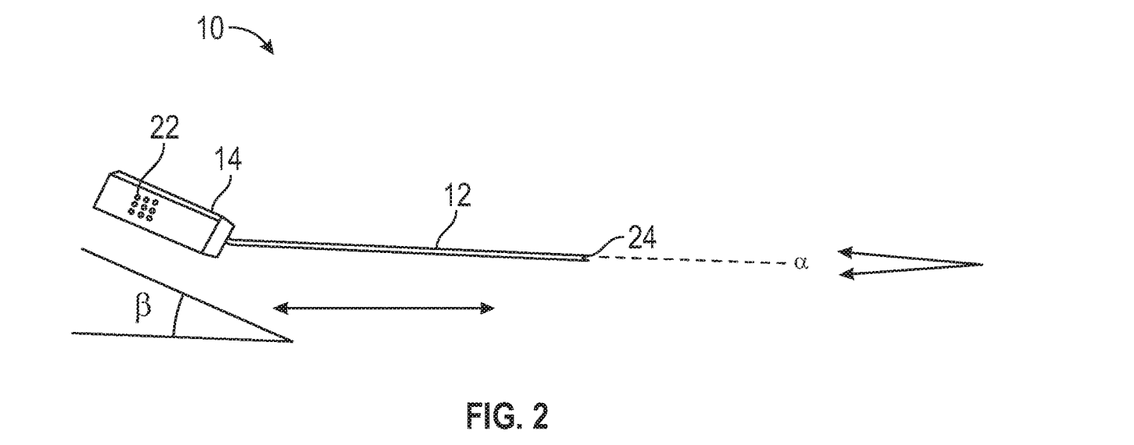
FIG. 2: Non-limiting schematic illustration of a needle for subcision procedures as seen from the side, depicting the handle disposed at an angle relative to the axis defined by the shaft of the needle.

As seen in FIG. 2, the handle 14 is disposed on the base end 16 of the shaft 12, at an angle β relative to the axis α. The angle β allows the surgeon to know the orientation of the needle underneath the patient's skin. The angle β can range from about 5 degrees to about 50 degrees, or from about 15 degrees to about 45 degrees. In one non-limiting example, the angle β is about 30 degrees. The preferred angle is determined by factors such as the particular procedure the needle 10 is to be used for, the anatomical location on the patient the procedure is to be performed, as well as the surgeon's general preferences. Considering these factors, angles greater than 50 degrees are possible and entirely encompassed within the scope of the present disclosure. Many different angles are possible, and the skilled person will recognize that the angle β can be adjusted as desired to accommodate subcision procedures to treat different anatomical locations. In some embodiments, the handle 14 is adjustable so as to be moveable between angles, and optionally being capable of being locked into place at a desired angle relative to the axis α.

The handle 14 is generally rectangular in cross-sectional shape, but may alternatively be cubic or other shapes suitable for grabbing and manipulating the needle 10. The handle 14 may optionally include grip-enhancing features or protrusions 22, such as ribs or teeth, to further enhance the user's grip. The handle 14 is manufactured from a suitable plastic or other material suitable for surgical instruments. In one non-limiting example, the handle 14 has a size of about one-inch by about one-inch, which is larger than the handle of a typical surgical needle. This enlarged handle 14, compared to conventional needle handles, enhances stability in the surgeon's hand. In use for a subcision procedure, as will be described in more detail below, the surgeon may hold the needle 10 by the handle 14 and move the needle 10 in the directions shown by the arrows in FIG. 2 to effectively cut scar tissue.

Figure 3A:
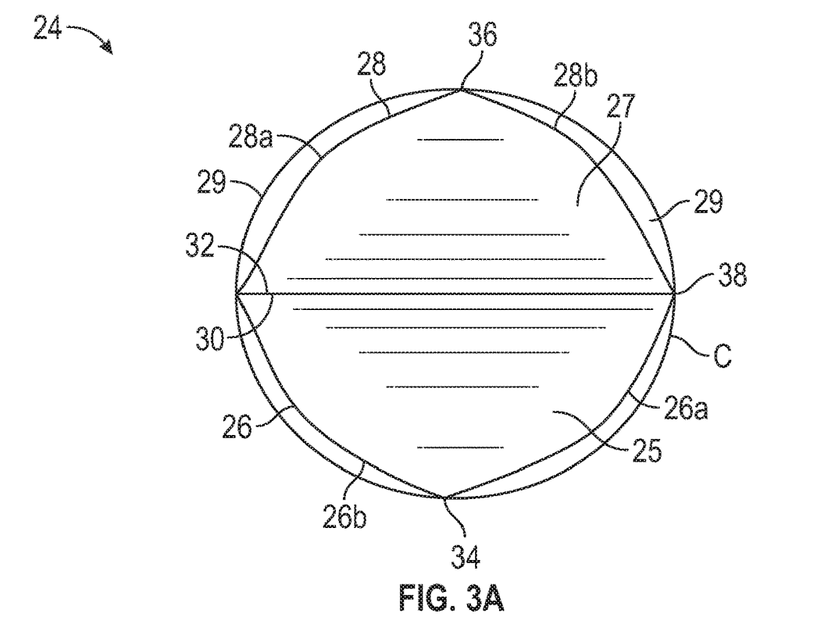
FIG. 3A shows an embodiment having two cutting edges in the concave cutting tip.

Referring now to FIG. 3A, the cutting end 18 of the shaft 12 may feature a concave cutting tip 24 having a first cutting edge 26 formed from a first face 25 and a second cutting edge 28 formed from a second face 27, where the first cutting edge 26 and the second cutting edge 28 are sharp inside edges configured for cutting tissue. The first and second cutting edges 26, 28 are referred to as inside edges because they are inside the circumference c defined by the outside surface 29 of the cutting tip 24. The outside surface 29 of the concave cutting tip 24 defines a circumference c of the concave cutting tip 24 which may or may not equal the circumference of the rest of the shaft 12. That is, in some embodiments, the shaft 12 may expand or narrow in circumference. In any event, the cutting edges 26, 28 are contained within the circumference c of the concave cutting tip 24, and therefore the sharp cutting edges 26, 28 are referred to as inside edges.

Referring still to FIG. 3A, the first cutting edge 26 is defined by the edge of the first face 25, and the second cutting edge 28 is defined by the edge of the second face 27. The concave cutting tip 24 pulls the scar tissue into the concavity and towards the axis α. In this manner, the concave cutting tip 24 feeds the scar tissue to the first cutting edge 26 and the second cutting edge 28, which facilitates cutting of the scar tissue. This is in contrast to some conventional needles which have a convex tip and push the scar tissue away from the needle. The cutting tip 24 is referred to as concave because, relative to the axis α, the cutting edges 26, 28 appear to be concave due to the recessed nature of the first face 25 and the second face 27. The first and second faces 25, 27 extend from the first and second edge bases 30, 32 to first and second terminus points 34, 36 in a concave manner relative to the axis α. The first cutting edge 26 is defined by the edge 26a of the first face 25 extending from the first edge base 30 to the first terminus point 34, and then the edge 26b extending from the first terminus point 34 to the first edge base 30 on the opposing side of the first terminus point relative to the edge 26a. The second cutting edge 28 is defined by the edge 28a of the second face 27 extending from the second edge base 32 to the second terminus point 36, and then the edge 28b extending from the second terminus point 36 to the second edge base 32 on the opposing side of the second terminus point 36 relative to the edge 28a. However, this is not meant to imply that the cutting edges 26, 28 are necessarily curved; rather, the cutting edges 26, 28 may be straight edges or may be curved edges.

Figure 4A:
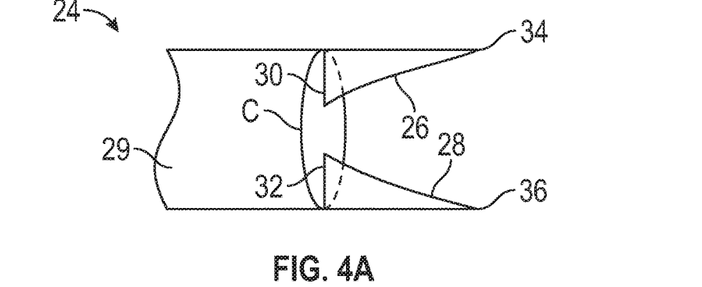

Although from the perspective of the axis α, the first and second faces 25, 27 extend from the first and second edge bases 30, 32 to first and second terminus points 34, 36, it may also be said that the first and second cutting edges 26, 28 extend from the first and second edge bases 30, 32 to the first and second terminus points 34, 36, since the first and second cutting edges 26, 28 are the edges of the recessed faces 25, 27. This is best seen from a side view, for example in FIGS. 4A-4D. Referring to FIGS. 4A-4D, the first and second cutting edges 26, 28 may extend from first and second edge bases 30, 32, which together may form a V-shaped apex 40, to first and second terminus points 34, 36 in a concave manner relative to the axis α. As seen in FIG. 4A, it is not necessary to have recessed faces; rather, the cutting tip 24 may include straight edges which extend from the edge bases 30, 32 to the terminus points 34, 36 in a concave manner relative to the axis α.

Figure 5:
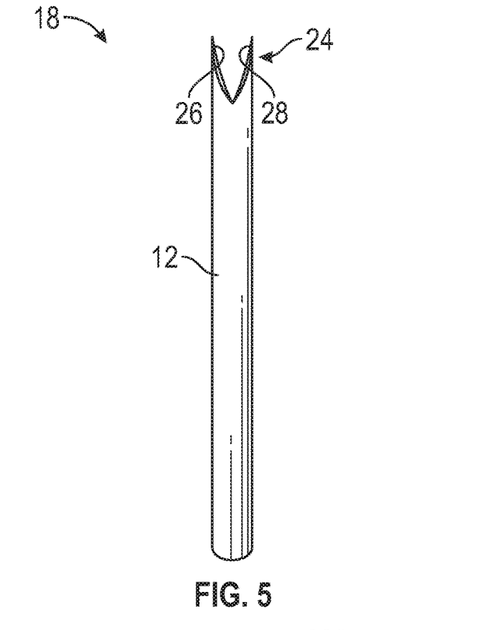
FIG. 5: Non-limiting example illustration of a part of a needle shaft with a concave cutting tip having first and second cutting edges.

The first and second cutting edges 26, 28 can be configured in any design suitable for cutting tissue within the concave cutting tip 24. In some embodiments, the concave cutting tip 24 is formed simply from two opposing bevelled edges to define the first and second cutting edges 26, 28, which may or may not be mirror images of each other, as depicted in FIG. 5. In the event the first and second cutting edges 26, 28 are not mirror images of each other, the handle 14 may contain an icon indicating the orientation of the concave cutting tip 24 to aid the surgeon in appropriately orienting the needle during subcision procedures. In some embodiments, the concave cutting tip 24 includes more than two cutting edges. For example, the concave cutting tip 24 may include three sharp inside cutting edges, or four sharp inside cutting edges. The number of sharp inside cutting edges is not particularly limited.

Figure 3B:
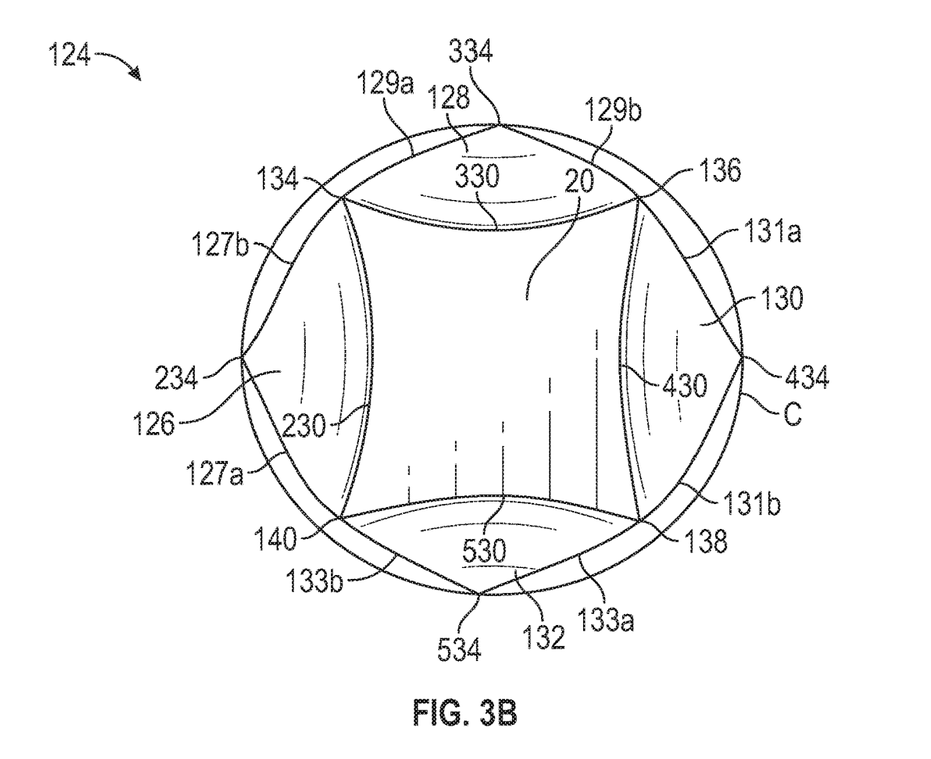
FIG. 3B shows an embodiment having four cutting edges in the concave cutting tip.
Figure 4B:
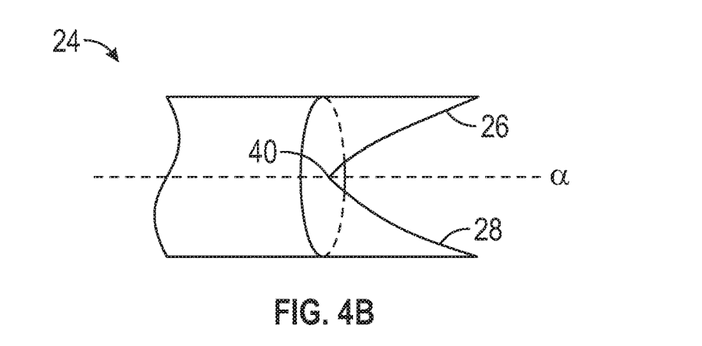
Figure 4C:
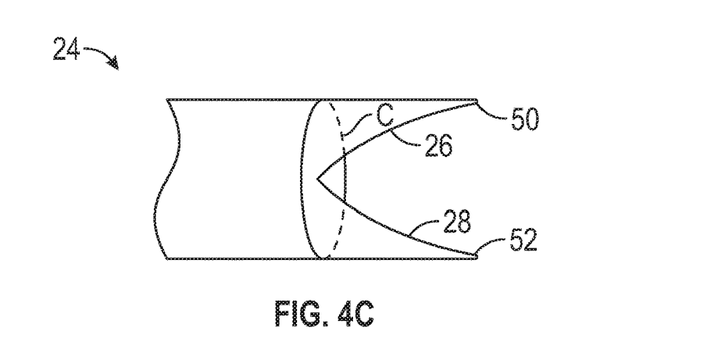
FIG. 4C shows an embodiment where the terminus points are rounded or dulled.
Figure 4D:
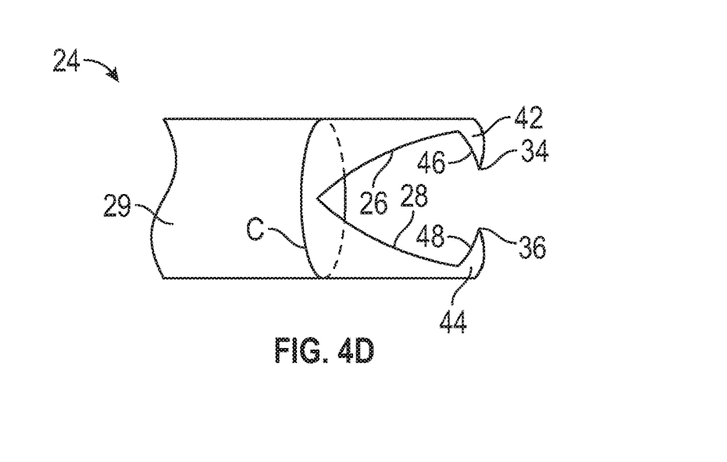
FIG. 4D shows an embodiment where the terminus points are at the ends of curls or hooks.

FIG. 3A illustrates an embodiment of the first cutting edge 26 and the second cutting edge 28 as seen from the front looking down the axis α. In some embodiments, the first edge base 30 and the second edge base 32 meet at a confluence point 38, as seen in FIGS. 3A, 4B-4D. In such cases, the first and second cutting edges 26, 28 may form a V-shaped apex 40 at the confluence point 38, as seen in FIGS. 4B-4D. This configuration is especially useful when the shaft 12 is solid (i.e., non-hollow). In other embodiments, such as where the shaft 12 is hollow, cutting edges can be formed around the central bore 20, as seen for example in FIG. 3B. In other embodiments, the first edge base 30 and the second edge base 32 do not meet, for example because of the central bore 20 between the edge bases 30, 32, as seen in FIGS. 3B, 4A. In any configuration, the cutting edges 26, 28 define sharp inside edges configured for cutting tissue.

In some embodiments, the first and second terminus points 34, 36 are at the ends of curled first and second tips 42, 44 which resemble hooks or claws, to better facilitate pulling of tissue by the concave cutting tip 24. An example of this is depicted in FIG. 4D. In such embodiments, as seen in FIG. 4D, a first auxiliary cutting edge 46 extends between the first terminus point 34 and the first cutting edge 26, and may be configured for cutting tissue, and a second auxiliary cutting edge 48 extends between the second terminus point 36 and the second cutting edge 28, and may be configured for cutting tissue. The first auxiliary cutting edge 46 and the second auxiliary cutting edge 48 are within the circumference c.

Referring now to FIG. 4C, the terminus points 34, 36 of the cutting edges 26, 28 may be dull or rounded off, though need not be. FIG. 4C illustrates an embodiment having a dulled first terminus point 50 and a dulled second terminus point 52. In other embodiments, the first and second terminus points 34, 36 may remain sharp.

The concave cutting tip 24 may include any desired number of sharp cutting edges. FIG. 3B illustrates an alternative embodiment of a concave cutting tip 124 where the concave cutting tip 124 includes four recessed faces which each define cutting edges: a first recessed face 126 which defines first cutting edges 127a, 127b, a second recessed face 128 which defines second cutting edges 129a, 129b, a third recessed face 130 which defines third cutting edges 131a, 131b, and a fourth recessed face 132 which defines fourth cutting edges 133a, 133b. In this embodiment, the first recessed face 126 meets the second recessed face 128 at a first confluence point 134, the second recessed face 128 meets the third recessed face 130 at a second confluence point 136, the third recessed face 130 meets the fourth recessed face 132 at a third confluence point 138, and the fourth recessed face 132 meets the first recessed face 126 at a fourth confluence point 140, where the first, second, third, and fourth confluence points 134, 136, 138, 140 surround the central bore 20. The first recessed face 126 extends from a first edge base 230 to a first terminus point 234, the second recessed face 128 extends from a second edge base 330 to a second terminus point 334, the third recessed face 130 extends from a third edge base 430 to a third terminus point 434, and the fourth recessed face 132 extends from a fourth edge base 530 to a fourth terminus point 534. Each of the first cutting edges 127a, 127b, second cutting edges 129a, 129b, third cutting edges 131a, 131b, and fourth cutting edges 133a, 133b are sharp and configured for cutting tissue. Each of the first cutting edges 127a, 127b, second cutting edges 129a, 129b, third cutting edges 131a, 131b, and fourth cutting edges 133a, 133b are within the circumference c, and are therefore inside edges. It is understood that many other configurations exist and are encompassed within the scope of the present disclosure, including embodiments where four cutting edges are present and the needle is non-hollow.

Figure 6A:
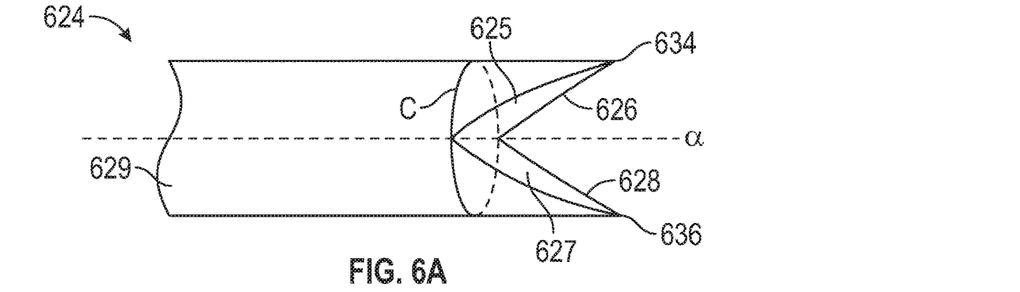
Figure 6B:
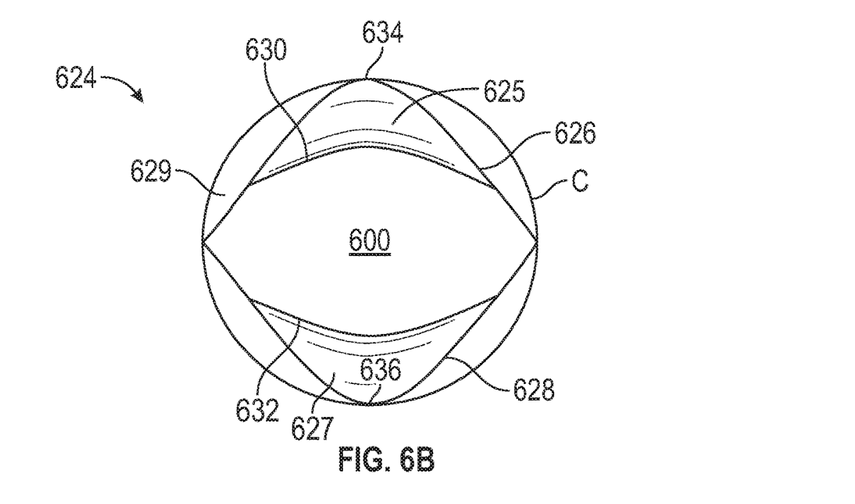
FIG. 6B shows the embodiment of FIG. 6A from the perspective of the axis α looking toward the concave cutting tip in which the door is visible.

Referring now to FIGS. 6A-6B, there is shown an embodiment of the concave cutting tip 624 which includes a door 600. The concave cutting tip 624 is formed from a first cutting edge 626 defined from a first recessed face 625 that extends from a first edge base 630 to a first terminus point 634, and a second cutting edge 628 defined from a second recessed face 627 that extends from a second edge base 632 to a second terminus point 636. FIG. 6B illustrates the first cutting edge 626 and the second cutting edge 628 as seen from the perspective looking down the axis α. A door 600 is contained within the circumference c of the concave cutting tip 624, and extends between the first edge base 630 and the second edge base 632. The door 600 may be depressed by force either from fluid contents being injected into the patient or from excised scar tissue debris pressing against the door 600 to be collected by the hollow interior of the needle 10. In another embodiment, the needle 10 may include a removable central core that can be removed to permit introduction of substances into the body or to collect and remove excised scar tissue debris.

FIGS. 7A-7E depict multiple embodiments of a concave cutting tip 724 that has multiple concavities. As shown in FIGS. 7A-7E, the concave cutting tip 724 has first, second, third, and fourth cutting edges 726, 728, 756, 758. The first, second, third, and fourth cutting edges 726, 728, 756, 758 are referred to as inside edges because they are generally contained within the circumference c defined by the outside surface 729 of the concave cutting tip 724. The first and second cutting edges 726, 728 are the outermost cutting edges because they are farther from the axis α than the third and fourth cutting edges 756, 758. The third and fourth cutting edges 756, 758 are the innermost cutting edges because they are positioned between the first cutting edge 726 and the second cutting edge 728 relative to the axis α.

As shown in FIGS. 7A-7E, the cutting tip 724 is referred to as concave because, relative to the axis α, the outermost cutting edges 726, 728 appear to be concave. In other words, the first and second cutting edges 726, 728 are defined by first and second recessed faces 725, 727 which extend from first and second edge bases 730, 732 to first and second terminus points 734, 736 in a concave manner relative to the axis α. For this reason, the cutting tip 724 is referred to as a concave cutting tip 724. However, this is not meant to imply that the cutting edges 726, 728, 756, 758 are necessarily curved; rather, the cutting edges 726, 728, 756, 758 may be straight edges or may be curved edges.

Figure 7A:
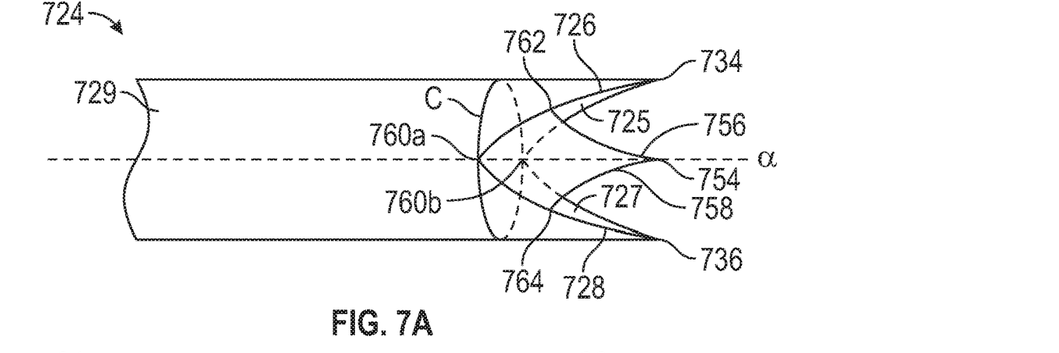
FIGS. 7A-7B show embodiments where the first, second, third, and fourth cutting edges define a major concavity and two minor concavities.
Figure 7B:
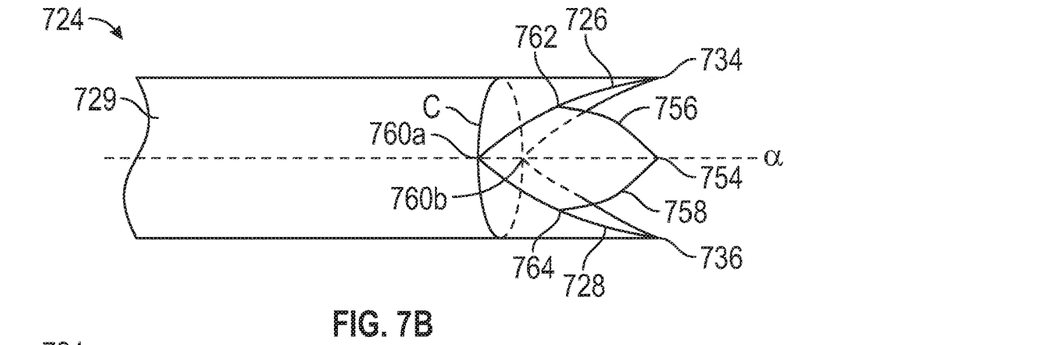

Referring now to FIGS. 7A-7B, the first and second edge bases of the first and second cutting edges 726, 728 meet at first confluence points 760a, 760b. A third cutting edge 756 and a fourth cutting edge 758 extend between the first and second cutting edges 726, 728. In these particular embodiments, the third cutting edge 756 extends from the first cutting edge 726 to a third terminus point 754 and the fourth cutting edge 758 extends from the second cutting edge 728 to the third terminus point 754 whereby the third terminus point 754 is formed by the intersection of the third cutting edge 756 with the fourth cutting edge 758. The first cutting edge 726 and the third cutting edge 756 meet at a second confluence point 762. The second cutting edge 728 and the fourth cutting edge 758 meet at a third confluence point 764. As can be seen in FIGS. 7A-7B, the third terminus point 754 is located between the first terminus point 734 and the second terminus point 736.

FIGS. 7A-7B also depict a major concavity and two minor concavities. The major concavity is formed by the first and second cutting edges 726, 728 as the first and second recessed faces 725, 727 and the first and second cutting edges 726, 728 extend from the first confluence points 760a, 760b to respective first and second terminus points 734, 736. A minor concavity is defined by the first and third cutting edges 726, 756 as the first and third cutting edges 726, 756 extend from the second confluence point 762 to respective first and third terminus points 734, 754. Another minor concavity is defined by the second and fourth cutting edges 728, 758 as the second and fourth cutting edges 728, 758 extend from the third confluence point 764 to respective second and third terminus points 736, 754. The major concavity is referred to as a major concavity because it is larger than the minor concavities and because it is concave with respect to the axis α. The major and minor concavities help the concave cutting tip 724 pull the scar tissue towards the axis α and against the first, second, third, and fourth cutting edges 726, 728, 756, 758 which facilitates cutting of the scar tissue.

Figure 7C:
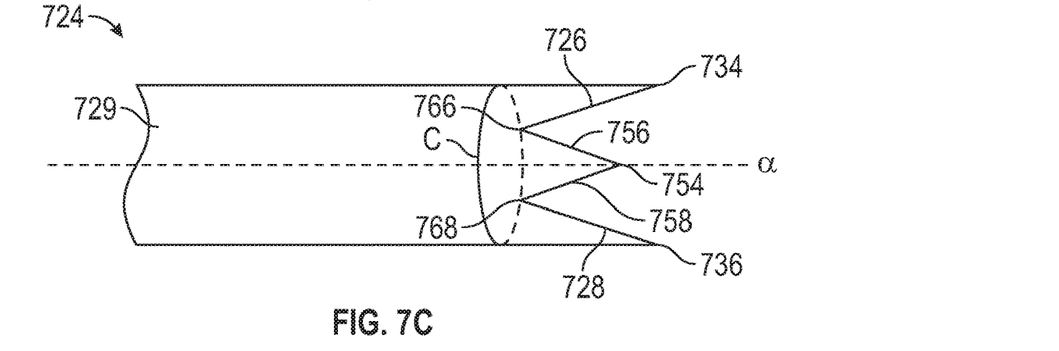
FIGS. 7C-7D show embodiments where the third terminus point is recessed with respect to the first and second terminus points.
Figure 7D:
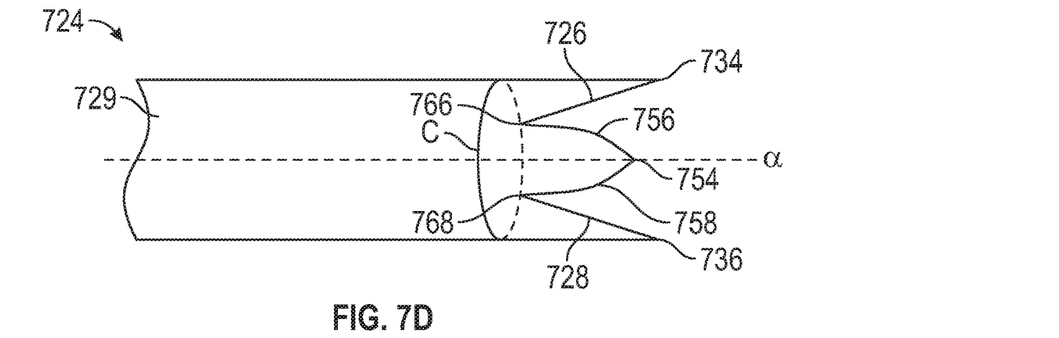

Referring now to FIGS. 7C-7D, the concave cutting tip 724 may include first, second, third, and fourth cutting edges 726, 728, 756, 758. The concave cutting tip 724 can be formed from a first cutting edge 726 that extends from a first edge base to a first terminus point 734, a second cutting edge 728 that extends from a second edge base to a second terminus point 736, a third cutting edge 756 that extends from a third edge base to a third terminus point 754, and a fourth cutting edge 758 that extends from a fourth edge base to a third terminus point 754. The third and fourth cutting edges 756, 758 extend between the first and second cutting edges 726, 728 until the third and fourth cutting edges 756, 758 converge at the third terminus point 754. The first cutting edge 726 and the third cutting edge 756 meet at a first confluence point 766. The second cutting edge 728 and the fourth cutting edge 758 meet at a second confluence point 768.

FIGS. 7C-7D also depict multiple concavities. A first concavity is defined by the first and third cutting edges 726, 756 as the first and third cutting edges 726, 756 extend from the first confluence point 766 to respective first and third terminus points 734, 754. A second concavity is defined by the second and fourth cutting edges 728, 758 as the second and fourth cutting edges 728, 758 extend from the second confluence point 768 to respective second and third terminus points 736, 754. The third terminus point 754 is located between the first terminus point 734 and the second terminus point 736. The third terminus point 754 is offset, or recessed, from the first and second terminus points 734, 736. This assists the concave cutting tip 724 in pulling the scar tissue into the first and second concavities and towards the axis α. In this manner, the concave cutting tip 724 feeds the scar tissue to the first, second, third, and fourth cutting edges 726, 728, 756, 758 which facilitates cutting of the scar tissue.

Figure 7E:
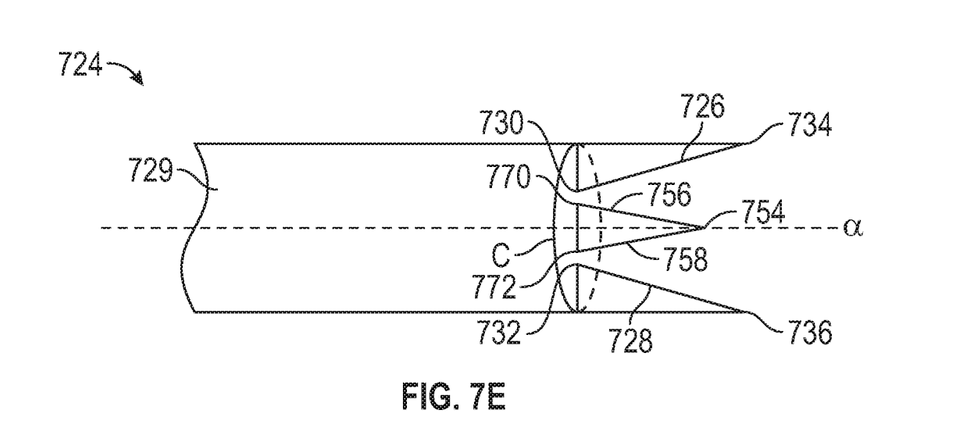
FIG. 7E shows an embodiment where none of the first, second, third, and fourth cutting edges meet at confluence points.

FIG. 7E depicts an embodiment of a concave cutting tip 724 in which none of the first, second, third, and fourth edge bases 730, 732, 770, 772 meet. In this configuration, there are no confluence points. The concave cutting tip 724 can be formed from a first cutting edge 726 that extends from a first edge base 730 to a first terminus point 734, a second cutting edge 728 that extends from a second edge base 732 to a second terminus point 736, a third cutting edge 756 that extends from a third edge base 770 to a third terminus point 754, and a fourth cutting edge 758 that extends from a fourth edge base 772 to a third terminus point 754. The third cutting edge 756 and fourth cutting edge 758 extend between the first and second cutting edges 726, 728 until the third and fourth cutting edges 756, 758 converge at the third terminus point 754.

FIG. 7E also depicts multiple concavities. A first concavity is defined by the first and third cutting edges 726, 756 as the first and third cutting edges 726, 756 extend from the cutting end to respective first and third terminus points 734, 754. A second concavity is defined by the second and fourth cutting edges 728, 758 as the second and fourth cutting edges 728, 758 extend from the cutting end to respective second and third terminus points 736, 754. The third terminus point 754 is located between the first terminus point 734 and the second terminus point 736. The third terminus point 754 is offset, or recessed, from the first and second terminus points 734, 736. This assists the concave cutting tip 724 in pulling the scar tissue into the first and second concavities and towards the axis α. In this manner, the concave cutting tip 724 feeds the scar tissue to the first, second, third, and fourth cutting edges 726, 728, 756, 758 which facilitates cutting of the scar tissue.

The cutting edges 726, 728, 756, 758 may be straight edges or curved edges. FIG. 7A depicts third 756 and fourth cutting edges 758 as curved edges with a concave shape relative to the axis α. FIGS. 7B, 7D depict third 756 and fourth cutting edges 758 as curved edges with a convex shape relative to the axis α. FIGS. 7C, 7E show third 756 and fourth cutting edges 758 as straight edges. While not illustrated in FIGS. 7A-7E, the first and second cutting edges 726, 728 may be curved.

The terminus points 734, 736, 754 of cutting edges 726, 728, 756, 758 are generally sharp, but they may be dull or rounded off. In FIGS. 7C-7E, the terminus point 754 is offset, or recessed, from the first and second terminus points 734, 736, although it does not have to be.

The concave cutting tip 24, 124, 624, 724 allows for scar tissue to be pulled inwards instead of pushed outwards during subcision scar removal procedures. In this manner, the surgeon only excises the scar tissue the cutting tip is being pushed against without disturbing anything else. The concave cutting tip 24, 124, 624, 724 also allows the needle 10 to be moved laterally without cutting skin. This is most conducive to performing subcision procedures, where one-way cutting is preferred. Lateral cutting is generally avoided in subcision procedures because lateral cutting does not cut the tissue in a way that causes the collagen bands to regrow correctly.

Figure 8A:
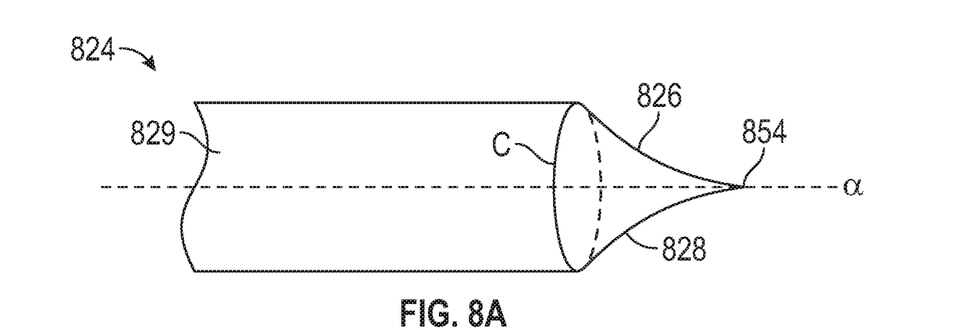
FIG. 8A shows an embodiment where the first and second cutting edges have a concave curvature relative to the axis α.
Figure 8B:
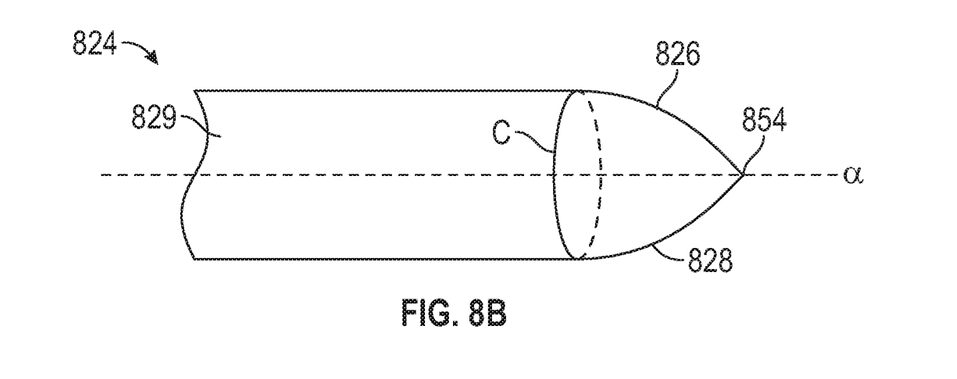
FIG. 8B shows an embodiment where the first and second cutting edges have a convex curvature relative to the axis α.

In alternative embodiments, the cutting tip is convex instead of concave. FIGS. 8A-8B depict two embodiments of a cutting tip 824 formed from two cutting edges 826, 828 extending from the outer surface 829, where FIG. 8A shows the cutting tip 824 as being concave relative to the axis α, and FIG. 8B shows the cutting tip 824 as being convex relative to the axis α. In FIGS. 8A-8B, the first cutting edge 826 and a second cutting edge 828 are contained within a circumference c defined by the outside surface 829 of the convex cutting tip 824, and are therefore inside edges. The first and second cutting edges 826, 828 extend from the outer surface 829 of the convex cutting tip 824 towards the axis α until the first and second cutting edges 826, 828 converge at the first terminus point 854. In FIG. 8A, the first and second cutting edges 826, 828 have a concave curvature relative to the axis α. In FIG. 8B, the first and second cutting edges 826, 828 have a convex curvature relative to the axis α.

Optionally, any of the cutting edges on the needle 10 may further include serrations for enhanced tissue cutting. Furthermore, like conventional hypodermic needles, the needle 10 may include smooth surfaces to prevent airborne pathogens from becoming trapped between irregularities in the needle's surfaces. However, it is not strictly necessary for the needle 10 to include smooth surfaces.

In general, the needle described herein can be made through a process similar to how conventional hypodermic needles are made. One such process is known as tube drawing, where a stainless steel tube is drawn through progressively smaller dies to form the shaft, and the end is then bevelled in the desired manner to create the cutting edges as described above. However, other methods of making the needle are possible, and are encompassed within the scope of the present disclosure. Regardless of number and configuration, the cutting edges can be made by bevelling the same piece of stainless steel, or other suitable material, used to make the shaft, in the desired shape or manner. Alternatively, the cutting tip can be manufactured separately from the shaft, and then connected to the shaft by suitable means such as welding.

As a general note, to reduce the risk of infection, the needle described herein may be made as a disposable, single use item. However, the present disclosure envisions embodiments that may be properly cleaned or sanitized and thus may be reusable.

The needle described herein can be used in any subcision procedure. One non-limiting example of a subcision procedure with the needle will be described, but it is understood that many different subcision procedures can be performed with the needle described herein. In general, the area to be treated is cleansed to remove dirt. Scar margins are defined, such as with a surgical marker, and local anaesthetic is administered. The needle is inserted at an acute angle adjacent to the scar with the cutting tip upwards and roughly parallel to the skin surface. Here, the bend between the handle and the needle (represented by the angle β) allows the needle to go under the skin and excise scar tissue with minimal tilting of the needle and without having to pull or manipulate the tissue. Moreover, the bend between the handle and the needle (represented by the angle β) allows the surgeon to know the orientation of the cutting surface while inside the patient and underneath the skin. The bend also makes it more difficult for the needle to rotate in the surgeon's hand while performing the subcision procedure by keeping the needle oriented in one direction.

Smaller gauge needle shafts may be used for small superficial scars and wrinkles. Once inserted, the needle is advanced through the dermis and moved back and forth, primarily in the directions depicted by the arrows in FIG. 2, and may be moved in a fan-like motion. The bend between the handle and the shaft helps prevent lateral cutting upon moving the needle in the skin. A snapping sound is heard as fibrous bands are transected in the deep dermis and deep dermal subcutaneous plane. Care is taken not to fan too deeply in a plane below the dermis. The needle can be rotated some amount, such as 90 degrees, and then moved again in a fan-like motion through the dermal scar. The needle is removed and squeezed circumferentially around the exit point to prevent large haematoma formation due to bleeding. Manual pressure is applied to the wound for several minutes.

It is understood that use of the needle described herein is not limited to subcision procedures. As noted above, the shaft of the needle does not need to be hollow, though it may be. Because the needle is used for cutting, it has a purpose distinct from that of a conventional hypodermic needle, which is to inject substances into the body. In embodiments where the shaft of the needle is hollow, the needle may be especially useful in procedures other than subcision procedures which utilize a needle for both cutting tissue and injecting substances into the body.

Certain embodiments of the needle and methods disclosed herein are defined in various example embodiments. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A needle comprising:
   a solid, non-hollow shaft defining an axis and extending between a base end and a cutting end;
   a handle disposed on the base end at an angle relative to the axis; and
   a concave cutting tip at the cutting end, wherein an outer surface of the concave cutting tip defines a circumference, and the concave cutting tip comprises a first cutting edge defined by a first recessed face extending from a first edge base to a first terminus point, and a second cutting edge defined by a second recessed face extending from a second edge base to a second terminus point, wherein the first cutting edge and the second cutting edge are each within the circumference.

2. The needle of claim 1, wherein the angle ranges from about 5 degrees to about 50 degrees.

3. The needle of claim 1, wherein the angle ranges from about 15 degrees to about 45 degrees.

4. The needle of claim 1, wherein the angle is about 30 degrees.

5. The needle of claim 1, wherein the first edge base and the second edge base meet to define a confluence point.

6. The needle of claim 5, wherein the confluence point defines a V-shaped apex between the first cutting edge and the second cutting edge.

7. The needle of claim 1, wherein the needle has a diameter corresponding to an 18-gauge needle or a 20-gauge needle.

8. The needle of claim 1, wherein the first cutting edge and the second cutting edge are each concave with respect to the axis.

9. The needle of claim 1, wherein the first and second terminus points are at the ends of curled tips.

10. A method of performing a subcision procedure, the method comprising using the needle of claim 1 to perform a subcision procedure on a patient.

11. A method of performing a subcision procedure, the method comprising:
    holding a needle having a cutting tip by a handle connected to the needle at an angle thereto, and inserting the needle into skin of a patient at an acute angle adjacent to a scar with the cutting tip substantially parallel to a skin surface, wherein the cutting tip comprises two or more sharp cutting edges interior to a circumference of the needle, and wherein the needle comprises a solid, non-hollow shaft extending between the cutting tip and the handle;
    advancing and moving the needle in a fan-like motion through the dermis so as to transect fibrous bands in the dermis with the cutting edges;
    rotating the needle and moving the needle in a fan-like motion through the scar; and
    removing the needle from the skin of the patient.

12. The method of claim 11, further comprising a step of cleaning an area around the skin prior to inserting the needle.

13. The method of claim 11, further comprising defining margins of the scar prior to inserting the needle.

14. The method of claim 11, further comprising administering a local anaesthetic to the patient prior to inserting the needle.

15. The method of claim 11, wherein the subcision procedure is a procedure to remove acne scars.

16. The method of claim 11, wherein the needle is squeezed circumferentially around an exit point to prevent large haematoma formation due to bleeding.

17. The method of claim 11, further comprising applying pressure to the skin where the needle was removed for a period of time.

* * * * *